(12) United States Patent
Tikanmäki et al.

(10) Patent No.: US 10,993,454 B2
(45) Date of Patent: May 4, 2021

(54) MILK-BASED PRODUCT AND A METHOD FOR ITS PREPARATION

(71) Applicant: VALIO LTD, Helsinki (FI)

(72) Inventors: Reetta Tikanmäki, Heksinki (FI); Olli Tossavainen, Espoo (FI); Matti Harju, Nummela (FI); Antti Heino, Helsinki (FI)

(73) Assignee: VALIO LTD., Helsinki (FI)

( * ) Notice: Subject to any disclaimer, the term of this patent is extended or adjusted under 35 U.S.C. 154(b) by 289 days.

(21) Appl. No.: 15/966,317

(22) Filed: Apr. 30, 2018

(65) Prior Publication Data

US 2018/0242608 A1  Aug. 30, 2018

Related U.S. Application Data

(62) Division of application No. 13/985,763, filed as application No. PCT/FI2012/050152 on Feb. 16, 2012, now abandoned.

(30) Foreign Application Priority Data

Feb. 18, 2011 (FI) ..................................... 20115156

(51) Int. Cl.
| A23C 21/06 | (2006.01) |
| A23C 9/12 | (2006.01) |
| A23C 9/142 | (2006.01) |
| A23C 9/15 | (2006.01) |
| A23J 1/20 | (2006.01) |
| A23J 3/08 | (2006.01) |
| A23L 5/20 | (2016.01) |
| A23L 33/19 | (2016.01) |
| A23K 20/147 | (2016.01) |
| A61K 35/20 | (2006.01) |

(52) U.S. Cl.
CPC ............ *A23C 21/06* (2013.01); *A23C 9/1206* (2013.01); *A23C 9/1422* (2013.01); *A23C 9/1425* (2013.01); *A23C 9/1512* (2013.01); *A23J 1/205* (2013.01); *A23J 3/08* (2013.01); *A23K 20/147* (2016.05); *A23L 5/273* (2016.08); *A23L 33/19* (2016.08); *A61K 35/20* (2013.01); *A23C 2210/206* (2013.01); *A23V 2002/00* (2013.01)

(58) Field of Classification Search
CPC ...... A23V 2002/00; A23V 2250/54246; A23V 2250/54252; A23V 2300/34; A23C 21/06; A23C 9/1512; A23C 2210/206; A23C 9/1206; A23C 9/1422; A23C 9/1425; A23C 21/00; A23C 21/10; A23C 9/142; A23C 9/152; A23J 1/205; A23J 3/08; A23J 1/20; A23J 3/10; A23K 20/147; A23K 10/28; A23L 33/19; A23L 5/273; A61K 35/20; A61P 3/02

See application file for complete search history.

(56) References Cited

U.S. PATENT DOCUMENTS

| 3,963,836 | A | 6/1976 | Henson et al. |
| 4,110,476 | A | 8/1978 | Rhodes |
| 4,309,417 | A | 1/1982 | Staples |
| 4,399,164 | A | 8/1983 | Lauck et al. |
| 4,702,923 | A | 10/1987 | Tokumaru et al. |
| 4,840,813 | A | 6/1989 | Greenberg et al. |
| 4,956,186 | A | 9/1990 | Streiff et al. |
| 5,085,874 | A | 2/1992 | Jungvid |
| 5,143,741 | A | 9/1992 | Podolski et al. |
| 5,169,666 | A | 12/1992 | Woychik |
| 5,350,590 | A | 9/1994 | McCarthy et al. |
| 5,373,779 | A | 12/1994 | Grusin |
| 5,503,865 | A | 4/1996 | Behringer et al. |
| 5,714,182 | A | 2/1998 | Bisson et al. |
| 6,303,160 | B1 | 10/2001 | Laye et al. |
| 6,399,140 | B1 | 6/2002 | Allen et al. |
| 6,406,736 | B1 | 6/2002 | Han |
| 6,485,762 | B1 | 11/2002 | Rizvi et al. |
| 7,579,029 | B2 | 8/2009 | Wolfschoon-Pombo et al. |
| 8,889,208 | B2 | 11/2014 | O'Mahony et al. |

(Continued)

FOREIGN PATENT DOCUMENTS

| AU | 771034 | 3/2004 |
| CA | 1 170 493 | 7/1984 |

(Continued)

OTHER PUBLICATIONS

Aisimo Corporation, "What is a KD (kiloDalton)" <accessed online May 2020; URL: aisimo.com/faq/membrane-filter/85.php>, Oct. 23, 2013, 1 page. (Year: 2013).*

Bulca, S. "Impact of casein and whey protein content on the renneting properties of UHT-treated microfiltrated milk concentrates" Milchwissenschaft—Milk Science International, 2009, 64(2), pp. 128-131. Coden: MILCAD. ISSN: 0026-3788; CAS Abstract only. (Year: 2009).*

(Continued)

*Primary Examiner* — Aaron J Kosar

(74) *Attorney, Agent, or Firm* — Nixon & Vanderhye P.C.

(57) ABSTRACT

The invention relates to a whey protein product having a ratio of whey protein to casein in the range from about 25:75 to about less than 50:50, a total protein content of at least 20% on dry matter basis, and a protein content of about 2.5 to about 8% by weight, based on the weight of the product. The product has a favourable amino acid composition and is especially suitable for athletes. The invention also relates to a method for producing a whey protein product, using microfiltration and ultrafiltration. The whey protein product is composed of the ultrafiltration retentate and a casein-containing material at a ratio of whey protein to casein of about 20:80 to about less than 50:50 and a total protein content of at least about 20% on dry matter basis.

25 Claims, 1 Drawing Sheet

(56) References Cited

U.S. PATENT DOCUMENTS

| | | |
|---|---|---|
| 2002/0192348 A1 | 12/2002 | Laye et al. |
| 2004/0151803 A1 | 8/2004 | Wolfschoon-Pombo et al. |
| 2005/0181095 A1 | 8/2005 | Achs |
| 2005/0214409 A1 | 9/2005 | Tossavainen et al. |
| 2006/0286252 A1 | 12/2006 | Rangavajla et al. |
| 2007/0104847 A1 | 5/2007 | O'Mahony |
| 2007/0128324 A1 | 6/2007 | Lowe |
| 2007/0134374 A1 | 6/2007 | Boenisch et al. |
| 2009/0047386 A1 | 2/2009 | Sweley et al. |
| 2010/0021595 A1 | 1/2010 | Bhaskar |
| 2010/0136134 A1 | 6/2010 | Boehm |
| 2010/0143538 A1 | 6/2010 | Bhaskar et al. |
| 2010/0303958 A1 | 12/2010 | Ur-Rehman et al. |
| 2011/0097442 A1 | 4/2011 | Harju et al. |
| 2012/0232023 A1 | 9/2012 | Harju et al. |

FOREIGN PATENT DOCUMENTS

| | | |
|---|---|---|
| CN | 1527669 | 9/2004 |
| CN | 1652690 | 8/2005 |
| CN | 1929749 | 3/2007 |
| CN | 101478891 | 7/2009 |
| CN | 102595915 | 7/2012 |
| CN | 102630803 | 8/2012 |
| EP | 0 283 101 | 9/1988 |
| EP | 0 608 525 | 8/1994 |
| EP | 0 631 731 | 1/1995 |
| EP | 1 815 747 | 8/2007 |
| FI | 20096114 | 4/2011 |
| FI | 20115156 | 8/2012 |
| JP | 2004-519229 | 7/2004 |
| JP | 2008-515440 | 5/2008 |
| JP | 2009-514511 | 4/2009 |
| JP | 2009-159947 | 7/2009 |
| JP | 2011-504365 | 2/2011 |
| NL | 189172 | 2/1993 |
| NZ | 511562 | 10/2003 |
| RU | 2 109 456 | 4/1998 |
| RU | 2 260 284 | 9/2005 |
| RU | 2 375 879 | 12/2009 |
| WO | WO 94/13148 | 6/1994 |
| WO | WO 96/08155 | 3/1996 |
| WO | WO 97/49295 | 12/1997 |
| WO | WO 00/30461 | 6/2000 |
| WO | WO 01/03515 | 1/2001 |
| WO | WO 01/22837 | 4/2001 |
| WO | WO 02/060279 | 8/2002 |
| WO | WO 03/007730 | 1/2003 |
| WO | WO 03/022063 | 3/2003 |
| WO | WO 03/094623 | 11/2003 |
| WO | WO 2005/016015 | 2/2005 |
| WO | WO 2005/087021 | 9/2005 |
| WO | WO 2005/110108 | 11/2005 |
| WO | WO 2006/105405 | 10/2006 |
| WO | WO 2007/051475 | 5/2007 |
| WO | WO 2008/063089 | 5/2008 |
| WO | WO 2008/127104 | 10/2008 |
| WO | WO 2008/136671 | 11/2008 |
| WO | WO 2009/068549 | 6/2009 |
| WO | WO 2009/108074 | 9/2009 |
| WO | WO 2010/044682 | 4/2010 |
| WO | WO 2010/114627 | 10/2010 |
| WO | WO 2011/051557 | 5/2011 |
| WO | WO 2011/099876 | 8/2011 |
| WO | WO 2012/110705 | 8/2012 |

OTHER PUBLICATIONS

McCarthy, N.A.; Wijayanti, H.B.; Crowley, S.V.; O'Mahony, J.A.; Fenelon, M.A. "Pilot-scale ceramic membrane filtration of skim milk for the production of a protein base ingredient for use in infant milk formula" International Dairy Journal, 2017(73), pp. 57-62; doi: 10.1016/j.idairyj.2017.04.010). (Year: 2017).*

European Notice of Opposition in Application No. 12710523.7 dated May 14, 2018 re Tine SA.

Evans et al. "Comparison of composition, sensory, and volatile components of thirty-four percent whey protein and milk serum protein concentrates" Journal of Daily Science, 92: 4773-4791 (2009).

Maubois, "Membrane microfiltration: a tool for a new approach in daily technology" The Australian Journal of Dairy Technology, vol. 57, No. 2: 92-96 (Jul. 2002).

Professor Emeritus Roger K. Abrahamsen, Curriculum Vitae, Apr. 30, 2018.

Professor Roger K. Abrahamsen, Expert Report, May 12, 2018.

Saboya et al., "Current developments of microfiltration technology in the daily industry" Lait, 80 (2000) 541-553, Review.

Office Action issued in KR Appln. No. 10-2019-7009241 dated May 28, 2019 (w/ translation).

Office Action issued in U.S. Appl. No. 12/607,367 dated Jun. 4, 2018.

Australian Patent Examination Report issued in Application No. 2012216966 dated May 5, 2015.

Augustin et al., "Use of Blends of Skim Milk and Sweet Whey Protein Concentrates in Reconstituted Yogurt" Australian Journal of Dairy Technology, Dairy Industry Association of Australia, vol. 58, No. 1, Apr. 1, 2003.

Belitz & Grosch, "Food Chemistry", Springer, ISBN: 3-540-64692-2, p. 473 (1999), $2^{nd}$ edition.

Beverages: Whey Protein, Tech Talk, CP Kelco, Issue 6, vol. 3, Dec. 2006, p. 1-6.

Chandan et al., Dairy Ingredients for Food Processing "Chapter 13—Fermented Dairy Ingredients", 2011 Blackwell Publishing Ltd, pp. 346-347.

Chinese Office Action issued in Appln. No. 201080048733.2 dated May 19, 2014 (w/ translation).

Chinese Office Action issued in Chinese App. No. 201280013400.5 dated Feb. 2, 2015 (with partial English translation).

Chinese Office Action w/English translation in CN 201280013400.5 dated Jun. 23, 2004.

Elsevier, Inc., Milk Proteins: From Expression to Food, Food Sci. and Tech. Intl. Series, 2009, p. 41-42.

Emerging Milk Protein Opportunities, Dairy Management Inc., May 2010, 8 pages.

European Notice of Opposition in Application No. 12710523.7 dated Apr. 8, 2015 in re Arla Foods Amba.

European Notice of Opposition in Application No. 12710523.7 dated Apr. 8, 2015 in re FrieslandCampina Nederland B.V.

European Notice of Opposition in Application No. 12710523.7 dated Apr. 8, 2015 in re N.V. Nutricia.

European Notice of Opposition in Application No. 12710523.7 dated Jan. 22, 2016 re Tine SA.

European Office Action issued in Appln. No. 10 781 921.1 dated Feb. 20, 2018.

Finnish Search Report for FI 20115156 dated Oct. 20, 2011.

Finnish Search Report for FI 20126278, dated Aug. 21, 2013.

Finnish Search Report in Serial No. 20096114 dated Apr. 29, 2010.

Goulas et al., "Applications of Membrane Separation," Advanced Dairy Science and Technology, Blackwell Publishing Ltd., 2008, pp. 55-62.

Ha et al., "Functional Properties of Whey, Whey Components, and Essential Amino Acids: Mechanisms Underlying Health Benefits for Active People (Review)," Journal of Nutritional Biochemistry, vol. 14, 2003, pp. 251-258.

Heino, "Opportunities and Challenges for Microfiltration in Dairy Processes," Valio Ltd, R&D, Separations of Value Added Products in the Food Industry, London, UK, Mar. 30, 2006, 6 pages.

Heino, A., et al., "Functional properties of native and cheese whey protein concentrate powders," Intl. Journal of Dairy Technology, vol. 60, No. 4, pp. 277-285, Nov. 2007.

Herbertz, et al., Milchserum—ein Rohstoff auch für Ihre Produkte?, Aus Technik Und Wissenschaft, 2006, p. 20-24.

International Preliminary Report on Patentability issued in PCT/FI2013/051143 dated Mar. 11, 2015, 14 pages.

International Search Report and Written Opinion of the International Searching Authority in PCT/FI2010/050843 dated Feb. 24, 2011.

(56) References Cited

OTHER PUBLICATIONS

International Search Report for PCT/FI2012/050152 dated Jun. 25, 2012.
International Search Report PCT/FI2013/051143, dated Feb. 27, 2014, 3 pages.
Isleten et al., "Effects of Dried Dairy Ingredients on Physical and Sensory Properties of Nonfat Yogurt," American Dairy Science Association, 2006, Journal Dairy Sci. 89:2865-2872.
Jang et al., "Advances in the biological effects of whey protein," *Food and Nutrition in China*, vol. 10: 49-51 (2008)**.
Japanese Office Action issued in Appln. No. 2012-535891 dated Jul. 15, 2014 (w/ translation).
Japanese Office Action issued in JP. Application No. 2013-553975 dated Sep. 1, 2015 (w/ part. trans.).
Kalab, "Yogurt: Electron Microscopy" Foods under the Microscope, Jun. 3, 2011. http://www.usu.edu/westcent/microstructure_food/Yogurt.htm.
Kiesner, et al., "Manufacturing of α-lactalbumin-enriched whey systems by selective thermal treatment in combination with membrane processes," 2000, Lait, vol. 80, p. 99-111.
Kücükcetin, A., "Effect of heat treatment and casein to whey protein ratio of skim milk on graininess and roughness of stirred yoghurt," Food Research International, 2008, vol. 41, p. 165-171.
Marafon, et al., "Effects of partially replacing skimmed milk powder with dairy ingredients on rheology, sensory profiling, and microstructure of probiotic stirred-type yogurt during cold storage," American Dairy Science Association, J. Dairy Sci., 2011, vol. 94, p. 5330-5340.
Marcelo, P. et al. "Physicochemical properties of liquid virgin whey protein isolate," Science Direct, Intl. Dairy Jnl., 18 (2008) 236-246.
Munchbach, et al., "Calcium Fortification in Dairy Products, Food Marketing & Tech.", Feb. 2010, p. 4.
Potočnik, et al., "Mare's milk: composition and protein fraction in comparison with different milk species; Mljekarstvo" 61(2), 2011, p. 107-113.
Puvanenthiran et al., "Structure and Visco-Elastic Properties of Set Yoghurt with Altered Casein to Whey Protein Ratios," International Dairy Journal, vol. 12, 2000, pp. 383-391.
Russian Office Action issued in Appln. No. 20121281886 dated Oct. 15, 2014 (w/ translation).
Russian Office Action issued in Appln. No. 2013142573 dated Mar. 28, 2016 (translated).
Russian Office Action issued in Appln. No. 2015126868/10 dated Nov. 16, 2017 (w/ translation).
Souci et al., "Food Composition and Nutrition Tables," MedPharm Sci. Publ., 7th Ed., pp. 154-155, 2008.
Tamime, A.Y. Robinson, R.K .. (2007). Tamime and Robinson's Yoghurt—Science and Technology (3rd Edition). Woodhead u Publishing. pp. 25, 32, 376-380 and 419-420 Online version available at: http://app.knovel.com/hotlink/toc/id:kpTRYSTE01/tamime-robinsons-yoghurt/tamime-robinsons-yoghurt.
U. Urho, maitotietoa. Tietoa Maidosta ja Ravitsemuksesta. Maito ja Terveys. Ry.: n julkaisu. 13. Painos, Marraskuu 2007.
VDI Verlag, "Proteinfraktionierung mittels Membrantrennverfahren by Martin Kersten, VDI Verlag GmbH, 2001" VDI Verlag, 2001 ISBN: 3-18-370903-1, pp. 1-5, 44-49, 116-123, 132-139.
Walstra, et al., "Chap 12. Membrane Processes," Dairy Sci. and Tech., Second Edition, 2006 Taylor & Francis Gp., pp. 341-356.
Walstra, et al., "Protein Preparations," Dairy Sci. and Tech., 2006 Taylor & Francis Gp., p. 540.
Walstra, et al., "Protein PreparationA1:A49s," Dairy Sci. and Tech., Second Edition, 2006 Taylor & Francis Gp., pp. 537-538.

* cited by examiner

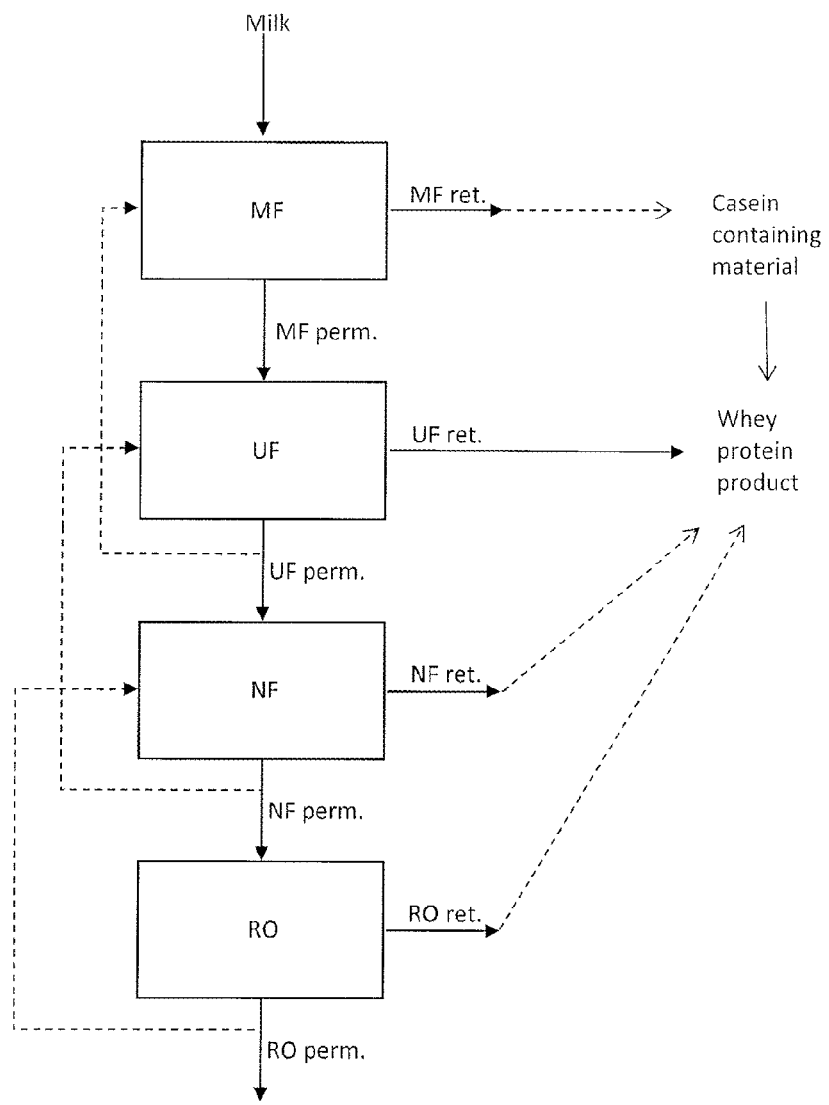

MILK-BASED PRODUCT AND A METHOD FOR ITS PREPARATION

This application is a divisional of U.S. application Ser. No. 13/985,763 filed Sep. 18, 2013, which is the U.S. national phase of International Application No. PCT/FI2012/050152 filed Feb. 16, 2012, which designated the U.S. and claims priority to FI 20115156 filed Feb. 18, 2011, the entire contents of each of which are hereby incorporated by reference.

FIELD OF THE INVENTION

The invention relates to a milk-based product enriched with whey protein and a method for the preparation thereof.

BACKGROUND OF THE INVENTION

It has been shown that the whey proteins are excellent protein sources, i.a. in nutrition of athletes, in increase and maintenance of muscle mass. Therefore, there are lots of whey protein powders, and beverages produced thereof in the market. In general, as a raw material for said whey protein products, a whey protein concentrate as a powder is used which is prepared by ultrafiltration of cheese, quark, or casein whey and by subsequent drying of the concentrate received from the ultrafiltration. These products have a problem that the taste is foul which results from proteolysis caused by starters such as cheese starters and a rennet, oxidation of residual fat, and other taste flaws. Also, removal of minerals during the production process of the whey products gives rise to a taste which is more watery than that of normal milk. It has been tried to eliminate the problems associated with the taste, whereby the whey products have been flavored up with various food additives, flavoring substances, flavoring preparations and processing aids.

In addition to the taste problems of the current whey protein products, there is a problem that all the whey proteins are not equal in their nutritive value. For example, nutritive value of glycomacropeptide released from casein into whey during the cheese production is minor than those of α-lactalbumin and β-lactoglobulin. Glycomacropeptide constitutes a significant portion of the total proteins of cheese whey.

Still a further problem arises from the high content of lactose included in the known whey products. As it is commonly known, lactose causes intolerance symptoms for a large amount of adult people in the world.

It is also generally known that thermal treatment of the whey protein based product causes structural faults in the product. These products are typically described as flaky, coarse, lumpy, or sandy.

In view of the above problems, price-quality ratio of the known whey protein products is not attractive. Consequently, the products are not commonly available in large scale but are provided for consumers as specialty products obtainable in restricted facilities, like fitness centers.

Milk-based whey protein products are generally widely known. Also, various membrane techniques and combinations thereof for separating milk components into individual fractions are largely described in the literature. For example, WO 94/13148 discloses a process for producing an undenatured whey protein concentrate by means of microfiltration and ultrafiltration of skim milk. Casein is retained in the microfiltration retentate while α-lactalbumin and β-lactoglobulin penetrate the microfiltration membrane having a pore size of about 0.1 microns quite easily.

WO 96/08155 discloses a separation of casein and whey proteins from a skim milk starting material utilizing microfiltration and ultrafiltration. For example, a milk beverage with a lowered whey protein content can be produced by the process.

WO 00/30461 discloses that microfiltration can be utilized in the preparation of infant formula to make the amino acid composition similar to that of human milk.

WO 03/094623 A1 discloses that several membrane techniques, i.e. ultrafiltration, nanofiltration and reverse osmosis, are utilized to prepare a lactose-free milk beverage.

It is desirable to provide whey protein products that do not possess the drawbacks of the known products but have a pleasant taste and favorable nutritive composition.

BRIEF DESCRIPTION OF THE INVENTION

We have surprisingly found that the problems associated with the known whey products can be avoided by including casein in the milk-based whey protein fraction prepared by membrane techniques and enriched with α-lactalbumin and β-lactoglobulin. It is surprising that even a small amount of casein is sufficient to improve the organoleptic properties of the product, like maintain the taste as smooth and velvety. Surprisingly, also the structure and stability of the whey protein product of the invention is good without any sand, flake, deposition or gel formation etc. Also, the nutritive value of the product is increased.

In an embodiment of the invention, it is possible to prepare a whey protein beverage that looks and tastes like milk but has a composition which is more favourable to athletes and other exercise enthusiasts.

BRIEF DESCRIPTION OF THE DRAWINGS

The FIGURE illustrates an embodiment of the method of the invention for producing a whey protein product.

DETAILED DESCRIPTION OF THE INVENTION

It is an object of the present invention to provide a whey protein product having a ratio of whey protein to casein in the range from about 25:75 to about less than 50:50, a total protein content of at least about 20% on dry matter basis, and a protein content of about 2.5% to about 8% by weight, based on the weight of the product. In an embodiment of the invention, the ratio of whey protein to casein ranges from about 25:75 to about 40:60. In a specific embodiment of the invention, said ratio is about 30:70. In further embodiments of the invention, said ratio is about 49:51, 48:52, 47:53, 46:54, and 45:55. In still further embodiments of the invention, said ratio is about 26:74, 27:73, 28:72, and 29:71.

In an embodiment of the invention, the total protein content of the product ranges from about 30% to about 60% on dry matter basis. In another embodiment, the total protein content ranges from 30% to 60% on dry matter basis. In a further embodiment of the invention, the total protein content is about 40% to about 60% on dry matter basis. In a still further embodiment, the total protein content is 40% to 60% on dry matter basis. In still another embodiment, the total protein content of the whey protein product is at least 20% on dry matter basis.

The whey protein product of the invention has good organoleptic properties and, specifically, is free from off-tastes caused by glycomacropeptides and the unpleasant metabolites present in conventional cheese, curd and casein whey. In addition, the whey protein product of the invention possesses favourable nutritive characteristics and favourable effect on health. Also, the stability of the whey protein product of the invention is good where no flakiness, settling, gelling or other phenomena causing undesirable changes in the structure is observed.

In the context of the present invention, the term "milk-based" means a product of milk origin, containing whey protein and casein.

The whey protein product can be prepared from one or more various components obtained from milk raw material by various membrane techniques or a combination thereof. The whey protein product can further comprise minerals of milk origin. The milk raw material can be milk as such or as a concentrate or pretreated as a desired manner. The milk raw material may be supplemented with ingredients generally used in the preparation of milk products, such as fat, protein or sugarfractions, or the like. The milk raw material may thus be, for instance, full-fat milk, cream, low-fat milk or skim milk, ultrafiltered milk, diafiltered milk, microfiltered milk, lactose-free or low-lactose milk, protease treated milk, recombined milk from milk powder, organic milk or a combination of these, or a dilution of any of these. Milk can originate from a cow, sheep, goat, camel, horse or any other animal producing milk suitable for nourishment. The milk is preferably low-fat or skim milk. In a more preferred embodiment of the invention, the whey protein product is prepared from skim milk.

The whey protein product of the invention can be provided as a liquid, like a beverage, a concentrate or a powder. In a specific embodiment of the invention, the whey protein product is a beverage. In an embodiment of the invention, a total protein content of the beverage is about 2.5% to about 8%, based on the weight of the beverage. In another embodiment, the total protein content of the beverage is 2.5% to 8%, based on the weight of the beverage. In a further embodiment, the total protein content of the beverage is about 3.5% to about 7%. In a still further embodiment, the total protein content of the beverage is 3.5% to 7%. The casein constitutes 75% to 50%, preferably 70% to 50% of the total protein content while the whey protein enriched with α-lactalbumin and β-lactoglobulin constitutes 25% to 50%, preferably 30% to 50%.

It is characteristic of the whey protein product of the invention that it contains no sugar, sweeteners or flavorings, however without limiting to this embodiment. In a specific embodiment of the invention, where the whey protein product is a beverage ready for instant use, no sugar, sweetener or flavoring is included in the beverage.

Like the mineral composition of cow's milk, the mineral composition of the whey protein product of the invention is highly physiological. For example, a whey protein beverage of the invention can typically contain 0.5% to 1.5%, preferably 0.6% to 0.8% of minerals. However, the calcium content of the whey protein product of the invention is lower that that of normal milk. The whey protein product can thus be provided with supplementary calcium and other milk minerals, for example, a nanofiltration permeate received from the method of the invention described below, in order to bring the calcium content to a level present in normal milk, or higher. Supplementary calcium can thus be provided as any calcium source, like milk calcium, calcium gluconate, calcium citrate, calcium lactate etc., or mixtures thereof.

Also fat can be included in the whey protein product of the invention. The fat content of the product typically ranges from about 0% up to 3.5%.

In an embodiment of the invention, the whey protein product is low-lactose or lactose-free. The low lactose or lactose-free product can be achieved by membrane techniques used for the preparation of the product. Also, any residual lactose in the whey protein product can be hydrolyzed by means of an enzyme. In the context of the invention, 'low lactose' means a lactose content of less than 1% in the whey protein product. 'Lactose free' means that the lactose content of the whey protein product is 0.5 g/serving (e.g. for liquid milks 0.5 g/244 g, the lactose content being at most 0.21%), however not more than 0.5%. In accordance with the invention, whey protein beverages containing little carbohydrate and having flawless organoleptic characteristics may also be produced.

The whey protein product of the invention can be used as a raw material in the preparation of all kinds of sour milk products and/or acidified fresh products, typically yoghurt, fermented milk, villi and fermented cream, sour cream, quark, butter milk, kefir, dairy shot drinks, and other sour milk products. We surprisingly found that the organoleptic properties of the sour milk products prepared from the whey protein product of the invention are similar to those of conventional sour milk products.

The products of the invention may be selected from, but are not limited to, the group consisting of food products, animal feed, nutritional products, food supplements, food ingredients, health food and pharmaceutical products. In an embodiment of the invention, the product is a food or feed product. In another embodiment of the invention, the product is functional food, i.e. food having any health promoting and/or disease preventing and/or alleviating properties. The form of each of the food product, food material, and/or the pharmaceutical products, and the animal feed is not particularly limited.

As stated above, due to its favorable nutritive composition the whey protein product of the invention is suitable for athletes and other exercise enthusiasts as such or as a part of a regular diet. The present invention provides a composition comprising whey protein for supporting and improving healthy eating. The product can also be useful especially in connection for alleviation and/or prevention of adult-onset diabetes, metabolic syndrome and sarcopenia.

Another object of the invention is to provide a use of the whey protein product as a food product, animal feed, nutritional product, food supplement, food ingredient, health food and pharmaceutical product. In an embodiment of the invention, the product is provided as a functional food and/or a nutritional product. In another embodiment, the product is provided as a pharmaceutical.

The whey protein product can be produced from one or more of the fractions obtained by means of membrane techniques. Two or more techniques can be combined, including microfiltration, ultrafiltration, nanofiltration, and reverse osmosis, in an appropriate manner.

A further object of the invention is thus to provide a method for producing a whey protein product which comprises subjecting a milk-based raw material to microfiltration to separate an ideal whey as a microfiltration permeate and a casein concentrate as a microfiltration retentate, subjecting at least a portion of the microfiltration permeate to ultrafiltration to provide an ultrafiltration permeate and a whey protein concentrate as an ultrafiltration retentate, composing a whey protein product from the ultrafiltration retentate and a casein-containing material so as to provide a ratio of whey protein to casein in the range of about 20:80 to about less than 50:50 and a total protein content of at least about 20% on dry matter basis, and if desired, from other ingredients.

The milk-based raw material is preferably skim milk.

Any material containing casein can be used as the casein-containing material in the present invention. In an embodiment of the invention, the casein-containing material is selected from a group consisting of the microfiltration retentate obtained in the method of the invention, milk, a sour milk product, an acidified milk product, a fermented milk product and any combination of these. The acidified milk product can be, for example, sour milk or yoghurt, or a combination of these. As used herein, the term "milk" means any normal secretion obtained from the mammary glands of mammals, such as cow's, goat's, camel's, horse's or sheep's milk, or any other animal producing milk suitable for nourishment. The milk can be supplemented with ingredients generally used in the preparation of milk products, such as fat, protein or sugar fractions, or the like. The milk thus include, for example, full-fat milk, low-fat milk or skim milk, cream, ultrafiltered milk (UF retentate), diafiltered milk, microfiltered milk (MF permeate), milk recombined from milk powder, organic milk or a combination or dilution of any of these. In an embodiment, the milk is skim milk. In another embodiment, the milk is low lactose or lactose-free milk.

In an embodiment of the invention, a whey protein product is produced having a ratio of whey protein to casein of about 25:75 to about less than 50:50. In another embodiment, the ratio is about 25:75 to about 40:60. In a further embodiment, the ratio is about 30:70.

In an embodiment, a whey protein product is produced having a total protein content of at least 20% on dry matter basis. In another embodiment, the total protein content ranges from about 30% to about 60% on dry matter basis. In a further embodiment, the total protein content is about 40% to about 60% on dry matter basis.

In an embodiment, a whey protein product prepared according to the method of the invention is a beverage having a protein content of about 2.5 to about 8% by weight, preferably about 3.5% to about 7%, based on the weight of the product.

After composing the whey protein product, it can be heat treated as a manner known per se, if appropriate.

In accordance with the invention, a milk-based raw material is subjected to microfiltration. At least a portion of the microfiltration permeate is then subjected to ultrafiltration. In an embodiment of the invention, at least a portion of the ultrafiltration permeate including majority of the minerals and sugars including lactose can further be subjected to nanofiltration (NF) to separate minerals into a NF permeate and sugars to NF retentate. In another embodiment, at least a portion of the NF permeate can be still further be subjected to reverse osmosis (RO) to concentrate the minerals into a RO retentate. These fractions obtained from said further membrane filtrations can be utilized to compose a whey protein product of the invention. In an embodiment of the invention, a microfiltration retentate, ultrafiltration retentate and nanofiltration retentate are used in the preparation of the whey protein product of the invention. In another embodiment, an ultrafiltration retentate and nanofiltration retentate are used in the preparation of the whey protein product of the invention. In still another embodiment of the invention, a microfiltration retentate, ultrafiltration retentate and reverse osmosis retentate are used in the preparation of the whey protein product of the invention. In an embodiment of the invention, the whey protein product is composed of milk, ultrafiltration retentate, nanofiltration retentate and water.

In a further embodiment of the invention, microfiltration (MF), ultrafiltration (UF) and/or nanofiltration (NF) are enhanced by diafiltration using water or a suitable fraction obtained from the membrane filtrations. When diafiltration is associated with microfiltration, an UF permeate obtained from the ultrafiltration of the MF permeate is suitably used as diawater. When the UF permeate is further subjected to nanofiltration, a NF permeate is suitably used as diawater in the ultrafiltration. When the NF permeate is still further subjected to reverse osmosis (RO), an RO permeate is suitably used as diawater in the nanofiltration. One or more of said diafiltration steps can be used in the method of the invention. Said fractions, and a combination of these can originate from a single process, or separate processes.

The method of the invention is illustrated in general terms in the FIGURE. Milk is subjected sequentially to microfiltration, ultrafiltration, nanofiltration, and reverse osmosis. Optional measures are indicated with a dash line in the FIGURE. Microfiltration, ultrafiltration and nanofiltration can be performed by diafiltration technique using at a least a portion of the ultrafiltration permeate, the nanofiltration permeate or the reverse osmosis (RO) permeate as diawater, respectively. The whey protein product of the invention is composed of the UF retentate and a casein containing material. If desired, the NF retentate and RO retentate can be introduced to the whey protein product. The casein containing material can include the MF retentate obtained from microfiltration. Also, the casein containing material can be composed entirely or partly of the MF retentate.

The method of the invention provides a whey protein product having good organoleptic properties, like taste and mouth-feel, with good stability. It is possible, by means of the method, to prevent the release of glycomacropeptides and metabolites causing unpleasant off-tastes for the whey protein product. It is thus possible to reduce, eliminate or mask the off-tastes of the whey protein product by performing the method of the invention.

The previous studies show that there are differences in nutritive quality of the whey proteins. More particularly, it has been discovered that α-lactalbumin has a more favorable nutritive value than β-lactoglobulin. Based on this knowledge, the composition of the whey protein product of the invention can be adjusted to various uses in an appropriate manner. In the present invention, the adjustment of the whey protein composition is achieved by a heat treatment of milk raw material, or by a selection of a membrane. The method of the invention uses a technique known per se in the heat treatment of milk products. Examples of heat treatments to be used in the method of the invention are pasteurization, high pasteurization, or heating at a temperature lower than the pasteurization temperature for a sufficiently long time. Specifically, UHT treatment (e.g. milk at 138° C., 2 to 4 s), ESL treatment (e.g. milk at 130° C., 1 to 2 s), pasteurization (e.g. milk at 72° C., 15 s), or high pasteurization (95° C., 5 min) can be mentioned. The heat treatment may be either direct (vapour to milk, milk to vapour) or indirect (tube heat exchanger, plate heat exchanger, scraped-surface heat exchanger).

In an embodiment of the invention, milk is subjected to a heat treatment at a temperature range of 65° C. to 95° C., for 15 seconds to 10 minutes prior to microfiltration to selectively separate the whey protein ingredients. As a result from the heat treatment, β-lactoglobulin is denaturated and associated with casein while α-lactalbumin passes through a membrane. In this way the content of the α-lactalbumin can be increased in the microfiltration permeate.

In an embodiment of the invention, lactose in the whey protein product of the invention is hydrolyzed into monosaccharides as is well known in the field. This can performed with commercially available lactase enzymes in a manner known per se. In an embodiment of the invention, the lactose hydrolysis is realized after the membrane filtrations on the composed whey protein product. In another embodiment of the invention, the lactose hydrolysis step and microfiltration step are initiated simultaneously with each other. In still another embodiment of the invention, the lactose hydrolysis of the milk raw material is initiated prior to membrane filtration step.

The lactose hydrolysis can continue as long as the lactase enzyme is inactivated, for example by a heat treatment of a whey protein product composed at a later stage of various fractions received in the method of the invention (UF retentate and MF retentate).

The following examples are presented for further illustration of the invention without limiting the invention thereto.

Example 1

Skim milk (1 000 L) is microfiltered by polymeric filtration membranes (Synder FR) having a pore size of 800 kDa. The concentration factor of 95 is used, including a diafiltration step. The concentration factor is calculated by Equation 1. The amount of microfiltration retentate formed is 190 L having a dry matter content of 20.0%.

$$\text{concentration factor}(-) = \left(\frac{\text{feed }(L)}{\text{retentate }(L)}\right) \times \left(\frac{\text{diafiltration feed }(L)}{\text{diafiltration retentate }(L)}\right) \quad (1)$$

The permeate formed in the microfiltration (1 890 L) is further filtered by polymeric ultrafiltration (UF) membranes (Koch HFK-131) having a pore size of 10 kDa. The permeate obtained from the ultrafiltration is further subjected to nanofiltration (NF) to give a NF retentate and permeate (130 L).

Ultrafiltration is performed by means of diafiltration using 130 L of the NF permeate above as diawater. The total concentration factor of the ultrafiltration is 24 (Equation 1). In the ultrafiltration, 100 L of ultrafiltration retentate and 1 920 L of ultrafiltration permeate are formed, of which 1 080 L is used for the diafiltration of the microfiltration. The remaining ultrafiltration permeate (840 L) is nanofiltered by filtration membranes (Desal 5-DK) having a cut-off value of 200 Da. The concentration factor of the nanofiltration is 4.25 (Equation 1), whereby 197 L of nanofiltration retentate and 644 L of nanofiltration permeate are formed, 130 L of the latter being used as diawater in the diafiltration of the ultrafiltration of the microfiltration permeate, as described above.

The residual nanofiltration permeate not used as diawater in the diafiltration of the ultrafiltration of the microfiltration permeate is used for other purposes or concentrated by reverse osmosis membranes (Koch HR) by using a concentration factor of 10 (Equation 1). The amount of reverse osmosis permeate of the nanofiltration permeate formed is 500 L, of which 44 L is used as diawater in the diafiltration of the nanofiltration. The amount of reverse osmosis retentate of the nanofiltration permeate formed is 55 L.

Example 2

Skim milk (1 000 L) is subjected to a heat treatment at a temperature range of 65° C. to 95° C., for 15 seconds to 10 minutes in a heat treatment apparatus to selectively separate the whey protein ingredients. The heat treatment of the skim milk influences the permeation of whey proteins in the microfiltration so that the microfiltration permeate is enriched with α-lactalbumin that is less thermolabile having denaturation degree of 0 to 26% while β-lactoglobulin is denatured to a degree of 1 to 90%. After the heat treatment of the skim milk, the milk is subjected to the filtration procedures as described in Example 1.

As an example, the proportion of α-lactalbumin of the total amount of α-lactalbumin and β-lactoglobulin (% by weight) in the microfiltration permeate was 38% (heat treatment of 75° C. for 30 seconds) to 45% (heat treatment of 90° C. for 30 seconds).

Example 3

A whey protein product according to the invention was composed from the microfiltration retentate, ultrafiltration retentate and nanofiltration retentate of Example 1, milk mineral powder and water as shown in Table 1. The whey protein to casein ratio of the product was 21:79 and the protein content was 52% on the dry matter basis. The product was a lactose-free milk drink in which the lactose was hydrolyzed enzymatically to a level of less than 0.1% after composing.

An educated expert panel evaluated the product organoleptically. The organoleptic properties were 'very good'. No taste flaws or structural faults affecting mouth-feel were observed.

TABLE 1

|  | MF retentate | UF retentate | NF retentate | Milk mineral powder | Water | Product 21:79 lactose-free |
|---|---|---|---|---|---|---|
| Portion (%) | 21 | 14 | 8 | 0.5 | 57 | 100 |
| Protein (%) | 15.3 | 5.8 | 0 | 0 | 0 | 4.0 |
| Wheyprotein (%) | 0.05 | 5.8 | 0 | 0 | 0 | 0.8 |
| Casein (%) | 15.2 | 0 | 0 | 0 | 0 | 3.2 |
| Lactose (%) | 4.2 | 3.9 | 17.5 | 45 | 0 | <0.1 |
| Ash (%) | 1.5 | 0.5 | 1.1 | 41 | 0.08 | 0.7 |

Whey protein products having a ratio of whey protein to casein of 22:78, 23:77, 24:76, and 25:75 can be prepared analogously from the same components by varying the amounts of each component accordingly.

Example 4

A whey protein product according to the invention was composed from the microfiltration retentate, ultrafiltration retentate and nanofiltration retentate of Example 1, milk mineral powder and water as shown in Table 2. The whey protein to casein ratio of the product was 25:75 and the protein content was 58% on the dry matter basis. The product was a lactose-free milk drink in which the lactose was hydrolyzed enzymatically to a level of less than 0.1% after composing.

An educated expert panel evaluated the product organoleptically. The organoleptic properties were 'very good'. No taste flaws or structural faults affecting mouth-feel were observed.

TABLE 2

|  | MF retentate | UF retentate | NF retentate | Milk mineral powder | Water | Product 25:75 lactose-free |
|---|---|---|---|---|---|---|
| Portion (%) | 25 | 22 | 5 | 0.4 | 47 | 100 |
| Protein (%) | 15.3 | 5.8 | 0 | 0 | 0 | 5.1 |
| Whey protein (%) | 0.05 | 5.8 | 0 | 0 | 0 | 1.3 |
| Casein (%) | 15.2 | 0 | 0 | 0 | 0 | 3.8 |
| Lactose (%) | 4.2 | 3.9 | 17.5 | 45 | 0 | <0.1 |
| Ash (%) | 1.5 | 0.5 | 1.1 | 41 | 0.08 | 0.7 |

Example 5

A whey protein product according to the invention was composed from the microfiltration retentate, ultrafiltration retentate and nanofiltration retentate of Example 1, and water as shown in Table 3. The whey protein to casein ratio of the product was 30:70 and the protein content was 56% on the dry matter basis.

An educated expert panel evaluated the product organoleptically. The organoleptic properties were 'very good'. No taste flaws or structural faults affecting mouth-feel were observed.

TABLE 3

|  | MF retentate | UF retentate | NF retentate | Water | Product 30:70 |
|---|---|---|---|---|---|
| Portion (%) | 32 | 36 | 12 | 20 | 100 |
| Protein (%) | 15.3 | 5.8 | 0 | 0 | 7.0 |
| Whey protein (%) | 0.05 | 5.8 | 0 | 0 | 2.1 |
| Casein (%) | 15.2 | 0 | 0 | 0 | 4.9 |
| Lactose (%) | 4.2 | 3.9 | 17.5 | 0 | 4.8 |
| Ash (%) | 1.5 | 0.5 | 1.1 | 0.08 | 0.8 |

Example 6

A whey protein product according to the invention was composed from the ultrafiltration retentate and nanofiltration retentate of Example 1, milk and water as shown in Table 4. The whey protein to casein ratio of the product was 40:60 and the protein content was 25% on dry matter basis.

An educated expert panel evaluated the product organoleptically. The organoleptic properties were 'very good'. No taste flaws or structural faults affecting mouth-feel were observed.

TABLE 4

|  | Milk | UF retentate | NF retentate | Water | Product 40:60 |
|---|---|---|---|---|---|
| Portion (%) | 56 | 11 | 10 | 23 | 100 |
| Protein (%) | 3.3 | 5.8 | 0 | 0 | 2.5 |
| Whey protein (%) | 0.7 | 5.8 | 0 | 0 | 1.0 |
| Casein (%) | 2.6 | 0 | 0 | 0 | 1.5 |
| Lactose (%) | 4.8 | 3.9 | 17.5 | 0 | 4.8 |
| Ash (%) | 0.8 | 0.5 | 1.1 | 0.08 | 0.6 |
| Fat (%) | 3.5 | 0 | 0 | 0 | 2.0 |

Example 7

A whey protein product according to the invention was composed from the ultrafiltration retentate and nanofiltration retentate of Example 1, milk and water as shown in Table 5. The whey protein to casein ratio was 49:51 and protein content was 38% on the dry matter basis. The product was a low lactose milk drink in which the lactose was hydrolyzed enzymatically after composing.

An educated expert panel evaluated the product organoleptically. The organoleptic properties were 'very good'. No taste flaws or structural faults affecting mouth-feel were observed.

TABLE 5

|  | Milk | UF retentate | NF retentate | Water | Product 49:51 low lactose |
|---|---|---|---|---|---|
| Portion (%) | 63 | 21 | 6 | 11 | 100 |
| Protein (%) | 3.3 | 5.8 | 0 | 0 | 3.3 |
| Whey protein (%) | 0.7 | 5.8 | 0 | 0 | 1.6 |
| Casein (%) | 2.6 | 0 | 0 | 0 | 1.7 |
| Lactose (%) | 4.8 | 3.9 | 17.5 | 0 | 0.8 |
| Ash (%) | 0.8 | 0.5 | 1.1 | 0.08 | 0.7 |

Whey protein products having a ratio of whey protein to casein of 48:52, 47:53, 46:54, and 45:55 can be prepared analogously from the same components by varying the amounts of each component accordingly.

The invention claimed is:

1. A method for producing a whey protein product which comprises
subjecting a milk-based raw material to microfiltration to separate an ideal whey as a microfiltration permeate and a casein concentrate as a microfiltration retentate,
subjecting at least a portion of the microfiltration permeate to ultrafiltration to provide an ultrafiltration permeate and a whey protein concentrate as an ultrafiltration retentate, composing a whey protein product from the ultrafiltration retentate and a casein-containing material so as to provide a ratio of whey protein to casein of about 20:80 to about less than 50:50 and a total protein content of at least about 20% on dry matter basis.

2. The method of claim 1 wherein the microfiltration is performed with a membrane having a pore size of 800 kDa.

3. The method of claim 1 wherein the ultrafiltration is performed with a membrane having a pore size of 10 kDa.

4. The method of claim 1 wherein the milk-based raw material is skim milk.

5. The method of claim 1 wherein the ratio of whey protein to casein of the whey protein product is about 25:75 to about less than 50:50.

6. The method of claim 1 wherein the total protein content ranges from about 30% to about 60% on dry matter basis.

7. The method of claim 1 wherein the product is a beverage having a protein content of about 2.5% to about 8% by weight, based on the weight of the product.

8. The method of claim 1 wherein the casein-containing material is selected from a group consisting of the microfiltration retentate, milk, a sour milk product, an acidified milk product, a fermented milk product and any combination of these.

9. The method of claim 1 wherein the ultrafiltration permeate is subjected to nanofiltration to provide a nanofiltration retentate and a nanofiltration permeate.

10. The method of claim 9 wherein the nanofiltration is performed with a membrane having a cut-off value of 200 Da.

11. The method of claim 9 wherein the nanofiltration permeate is subjected to reverse osmosis to provide a reverse osmosis retentate and a reverse osmosis permeate.

12. The method of claim 9 wherein the microfiltration retentate, ultrafiltration retentate and nanofiltration retentate are used for composing the whey protein product.

13. The method of claim 1 wherein diafiltration is used with microfiltration, ultrafiltration and nanofiltration.

14. The method of claim 1 wherein the milk-based raw material is subjected to a heat treatment at a temperature range of 65° C. to 95° C. for 15 seconds to 10 minutes prior to microfiltration.

15. The method of claim 1 wherein supplementary milk minerals are added to the whey protein product.

16. The method of claim 1 wherein the release of glycomacropeptides in the whey protein product is prevented.

17. The method of claim 1 wherein the off-taste of the whey protein product is reduced, eliminated or masked.

18. The method of claim 1 wherein no sugar, sweetener or flavorings are added to the whey protein product.

19. The method of claim 1 comprising a lactose hydrolysis step.

20. The method of claim 1 wherein the whey protein product contains less than 1% of lactose.

21. The method of claim 1 wherein the ratio of whey protein to casein of the whey protein product is about 25:75 to about 40:60.

22. The method of claim 1 wherein the ratio of whey protein to casein of the whey protein product is about 30:70.

23. The method of claim 1 wherein the total protein content ranges from about 40% to about 60% on dry matter basis.

24. The method of claim 1 wherein the product is a beverage having a protein content of about 3.5% to about 7% based on the weight of the product.

25. The method of claim 1 wherein the whey protein product contains not more than 0.5% of lactose.

* * * * *